United States Patent [19]
Lin et al.

[11] Patent Number: 5,869,658
[45] Date of Patent: Feb. 9, 1999

[54] PHOTOCHROMIC INDENO-FUSED NAPTHO [2,1-B]PYRANS

[75] Inventors: Jibing Lin; Barry Van Gemert, both of Murrysville, Pa.

[73] Assignee: PPG Industries, Inc., Pittsburgh, Pa.

[21] Appl. No.: 990,890

[22] Filed: Dec. 15, 1997

[51] Int. Cl.$^6$ .................... C07D 311/78; C07D 405/02; C07D 413/02; G02B 5/23
[52] U.S. Cl. ................. 544/106; 252/586; 546/192; 546/269; 549/49; 549/60; 549/382; 549/469; 549/472; 428/423.1; 428/423.7; 428/425.6; 428/473.5
[58] Field of Search ................. 549/382, 49, 60, 549/469, 472; 544/106; 546/269, 192; 252/586; 428/423.1, 423.7, 425.6, 473.5

[56] References Cited

U.S. PATENT DOCUMENTS

| | | | |
|---|---|---|---|
| 3,361,706 | 1/1968 | Meriwether et al. | 260/39 |
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Cassella et al. | 252/300 |
| 4,215,010 | 7/1980 | Hovey et al. | 252/300 |
| 4,342,668 | 8/1982 | Hovey et al. | 252/586 |
| 4,360,653 | 11/1982 | Stevens et al. | 526/301 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/586 |
| 4,931,220 | 6/1990 | Haynes et al. | 252/586 |
| 4,994,208 | 2/1991 | McBain et al. | 252/586 |
| 5,066,818 | 11/1991 | Van Gemert et al. | 549/389 |
| 5,200,483 | 4/1993 | Selvig | 526/301 |
| 5,238,981 | 8/1993 | Knowles | 524/110 |
| 5,274,132 | 12/1993 | Van Gemert | 549/389 |
| 5,373,033 | 12/1994 | Toh et al. | 822/96 |
| 5,384,077 | 1/1995 | Knowles | 252/586 |
| 5,405,958 | 4/1995 | Van Gemert | 544/71 |
| 5,429,774 | 7/1995 | Kumar | 252/586 |
| 5,458,814 | 10/1995 | Kumar et al. | 252/586 |
| 5,466,398 | 11/1995 | Van Gemert et al. | 252/586 |
| 5,475,074 | 12/1995 | Matuoka et al. | 526/336 |
| 5,514,817 | 5/1996 | Knowles | 549/384 |
| 5,552,090 | 9/1996 | Van Gemert et al. | 252/586 |
| 5,552,091 | 9/1996 | Kumar | 252/586 |
| 5,565,147 | 10/1996 | Knowles et al. | 252/586 |
| 5,573,712 | 11/1996 | Kumar et al. | 252/586 |
| 5,578,252 | 11/1996 | Van Gemert et al. | 252/586 |
| 5,645,767 | 7/1997 | Van Gemert . | |
| 5,651,923 | 7/1997 | Kumar et al. . | |

OTHER PUBLICATIONS

Olah et al., *Friedel–Crafts and Related Reactions,* Interscience Publishers, vol. 3, Chapter XXXI ("Aromatic Ketone Synthesis"), pp.1–8, 1964.

Ishihara et al., "Regioselective Friedel–Drafts Acylation of 1,2,3,4–Tetrahydroquinoline and Related Nitrogen Heterocycles: Effect on NH Protective Groups and Ring Size", J. Chem. Soc. Perkins Trans. 1, 1992, pp. 3401–3406.

*Primary Examiner*—Johann Richter
*Assistant Examiner*—Taofiq A. Solola
*Attorney, Agent, or Firm*—Irwin M. Stein; Frank P. Mallak

[57] ABSTRACT

Described are novel photochromic indeno-fused naphthopyran compounds having certain substituents at the 2-position of the pyran ring and an alkoxy group at the number 6 carbon atom. Certain other substituents may also optionally be present at the number 5, 7, 8, 9, 10, 11, 12 or 13 carbon atoms of the compounds. These compounds may be represented by the following graphic formula:

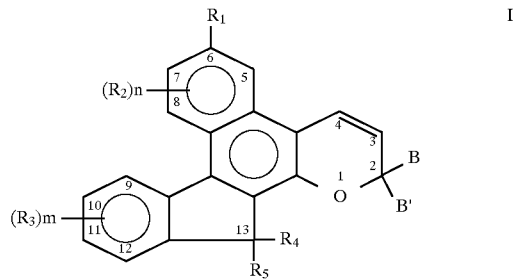

Also described are certain novel indeno-fused naphthols which are used to make the novel naphthopyran compounds. Further described are polymeric organic host materials that contain or that are coated with the novel naphthopyran compounds, or combinations thereof with complementary photochromic compounds, e.g., certain other naphthopyrans, benzopyrans, and spiro(indoline)type compounds.

22 Claims, No Drawings

PHOTOCHROMIC INDENO-FUSED NAPTHO [2,1-B]PYRANS

DESCRIPTION OF THE INVENTION

The present invention relates to certain novel naphthopyran compounds. More particularly, this invention relates to novel photochromic indeno-fused naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions. U.S. Pat. No. 5,645,767 describes photochromic indeno-fused naphtho[1,2-b]pyrans having activated colors ranging from orange to blue/gray.

The present invention relates to novel substituted indeno [1'2':4,3]naphtho[2,1-b]pyran compounds having certain substituents at the 2-position of the pyran ring. The invention further includes certain novel 7H-benzo[c]fluoren-6-ol compounds. The naphtho[2,1-b]pyrans of the present invention exhibit activated colors ranging from yellow to orange. Photochromic compounds of the present invention include compounds that exhibit acceptable photochromic performance properties, i.e., activated intensity, coloration rate and fade rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel indeno-fused naphtho[2,1-b]pyrans having activated colors ranging from yellow to orange may be prepared. These compounds may be described as indeno[1'2':4,3]naphtho[2,1-b]pyrans having certain substituents at the 2 position of the pyran ring and an alkoxy group at the number 6 carbon atom of the naphthopyran compound. Certain other substituents may optionally also be present at the number 5, 7, 8, 9, 10, 11, 12 or 13 carbon atoms of the naphtho portion of the compounds. These compounds may be represented by the following graphic formula I in which the numbers 1 through 13 within the depicted ring system represent the numbers of the ring atoms of the indenonaphthopyran:

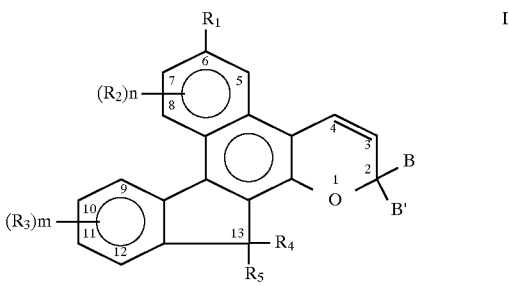

In graphic formula I, $R_1$ is $C_1$–$C_6$ alkoxy, preferably $C_1$–$C_3$ alkoxy. Each $R_2$ may be $C_1$–$C_6$ alkyl, $C_1$–$C_6$ alkoxy, chloro or fluoro, and n is the integer 0, 1, or 2. Each $R_3$ may be $C_1$–$C_6$ alkyl, chloro or fluoro, and m is the integer 0, 1 or 2. When m and n are 2, the $R_2$ (and $R_3$) substituents may each be the same or different. More preferably, $R_2$ is $C_1$–$C_3$ alkyl, $C_1$–$C_3$ alkoxy, or fluoro, n is the integer 0 or 1, $R_3$ is $C_1$–$C_3$ alkyl or fluoro and m is the integer 0 or 1. Most preferably, $R_2$ is $C_1$–$C_3$ alkyl or $C_1$–$C_3$ alkoxy, n is the integer 0 or 1 and m is 0.

$R_4$ and $R_5$ in graphic formula I may together form an oxo group, or $R_4$ and $R_5$ may each be hydrogen, hydroxy, $C_1$–$C_6$ alkyl, $C_3$–$C_7$ cycloalkyl, allyl, phenyl, mono-substituted phenyl, benzyl, mono-substituted benzyl, or $R_4$ and $R_5$ may each be the group, —$OR_6$, wherein $R_6$ is $C_1$–$C_6$ alkyl, phenyl($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl or allyl, each of the aforedescribed phenyl and benzyl group substituents being $C_1$–$C_6$ alkyl or $C_1$–$C_6$ alkoxy.

More preferably, $R_4$ and $R_5$ may each be hydrogen, hydroxy, $C_1$–$C_4$ alkyl, $C_3$–$C_6$ cycloalkyl, chloro, fluoro or the group, —$OR_6$, wherein $R_6$ is $C_1$–$C_3$ alkyl, phenyl ($C_1$–$C_2$)alkyl, mono($C_1$–$C_3$)alkyl substituted phenyl ($C_1$–$C_3$)alkyl, mono($C_1$–$C_3$)alkoxy substituted phenyl ($C_1$–$C_3$)alkyl, $C_1$–$C_3$ alkoxy($C_2$–$C_4$)alkyl, $C_1$–$C_3$ chloroalkyl or $C_1$–$C_3$ fluoroalkyl. Most preferably, $R_4$ and $R_5$ are each hydrogen, hydroxy, $C_1$–$C_4$ alkyl or the group, —$OR_6$, wherein $R_6$ is $C_1$–$C_3$ alkyl.

B and B' in graphic formula I may each be selected from the group consisting of:
(i) the unsubstituted, mono-, di-, and tri-substituted aryl groups, phenyl and naphthyl;
(ii) the unsubstituted, mono- and di-substituted heteroaromatic groups pyridyl, furanyl, benzofuran-2-yl, benzofuran-3-yl, thienyl, benzothien-2-yl, benzothien-3-yl, each of said aryl and heteroaromatic substituents in parts (i) and (ii) being selected from the group consisting of hydroxy, amino, mono($C_1$–$C_6$) alkylamino, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy ($C_1$–$C_4$)alkyl, acryloxy, methacryloxy, chloro and fluoro;

(iii) the groups represented by the following graphic formulae:

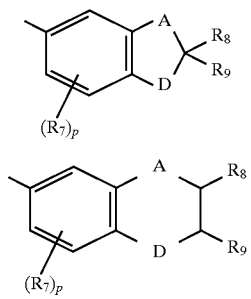

wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_7$ is $C_1$–$C_6$ alkyl, $C_1$–$C_6$ alkoxy, hydroxy, chloro or fluoro; $R_8$ and $R_9$ are each hydrogen or $C_1$–$C_6$ alkyl; and p is the integer 0, 1, or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl ($C_3$–$C_6$)cycloalkyl, chloro($C_3$–$C_6$)cycloalkyl, and fluoro($C_3$–$C_6$)cycloalkyl; and (v) the group represented by the following graphic formula:

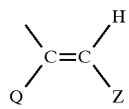

wherein Q in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl, and thienyl, each of said group substituents in this part (v) being $C_1$–$C_4$ alkyl, $C_1$–$C_4$ alkoxy, fluoro, or chloro; or (vi) B and B' taken together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1] heptylidene, i.e., bornylidene, bicyclo[3.2.1]octylidene, bicyclo[3.3.1]nonan-9-ylidene, bicyclo[4.3.2] undecane, and saturated $C_7$–$C_{12}$ spiro-tricyclic hydrocarbon rings, e.g., tricyclo[2.2.1.0 2,6] heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of: (i) phenyl, mono-substituted phenyl, and di-substituted phenyl, preferably substituted in the meta and/or para positions; (ii) the unsubstituted, mono- and di-substituted heteroaromatic groups furanyl, benzofuran-2-yl, thienyl, and benzothien-2-yl, each of said phenyl and heteroaromatic substituents being selected from the group consisting of hydroxy, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIA and IIB, wherein A is carbon and D is oxygen, $R_7$ is $C_1$–$C_3$ alkyl or $C_1$–$C_3$ alkoxy, $R_8$ and $R_9$ are each hydrogen or $C_1$–$C_4$ alkyl; and p is the integer 0 or 1; (iv) $C_1$–$C_4$ alkyl; and (v) the group represented by the graphic formula IIC wherein Q is hydrogen or methyl and Z is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of (i) phenyl, mono- and di-substituted phenyl, (ii) the unsubstituted, mono- and di-substituted heteroaromatic groups furanyl, benzofuran-2-yl, thienyl, and benzothien-2-yl, each of said phenyl and heteroaromatic substituents being selected from the group consisting of hydroxy, $C_1$–$C_3$ alkyl, $C_1$–$C_3$ alkoxy, fluoro and chloro; and (iii) the group represented by graphic formula IIA, wherein A is carbon and D is oxygen, $R_7$ is $C_1$–$C_3$ alkyl or $C_1$–$C_3$ alkoxy, $R_8$ and $R_9$ are each hydrogen or $C_1$–$C_3$ alkyl, and p is the integer 0 or 1; or (iv) B and B' taken together form fluoren- 9-ylidene, adamantylidene, bornylidene, norbornylidene, or bicyclo[3.3.1]nonan-9-ylidene.

The present invention further includes certain precursor compounds to the compound represented by graphic formula I. In particular, it has now been discovered that certain novel indeno-fused naphthols may be prepared. These compounds may be described as 7H-benzo[c]fluoren-6-ol compounds having an alkoxy group at the 3 position of the naphthol ring. Certain other substituents may also optionally be present at the number 1, 2, 4 and 8–11 carbon atoms of the compounds. These additional compounds may be represented by the following graphic formula I' wherein $R_1$, $R_2$ and $R_3$, n and m are as defined above with respect to graphic formula I.

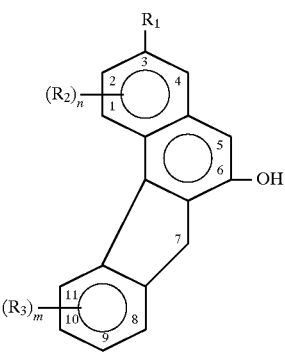

Compounds represented by graphic formula I may be prepared by the following Reactions A through F. Compounds represented by graphic formula I' may be prepared according to Reactions C and D. Compounds represented by graphic formula V or VA are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent possible phenyl substituents.

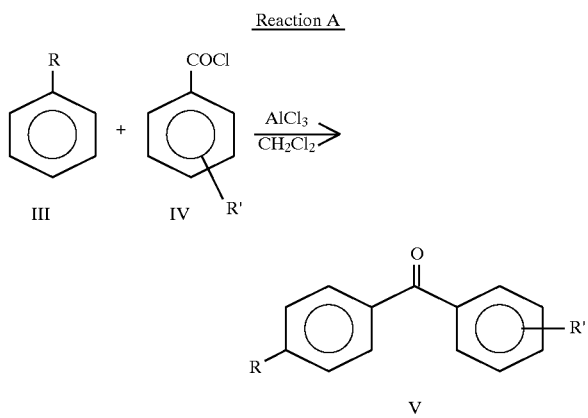

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68, which disclosure is incorporated herein by reference.

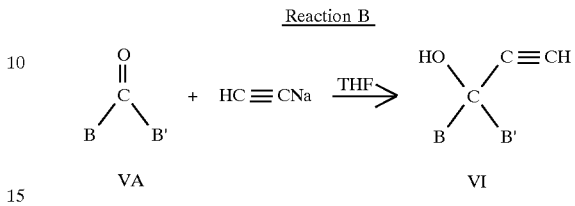

In Reaction C, the compounds represented by graphic formula VII, some of which are commercially available, are condensed with methanol in the presence of a catalytic amount of an acid such as sulfuric acid to form the corresponding phenyl acetate represented by graphic formula VIII.

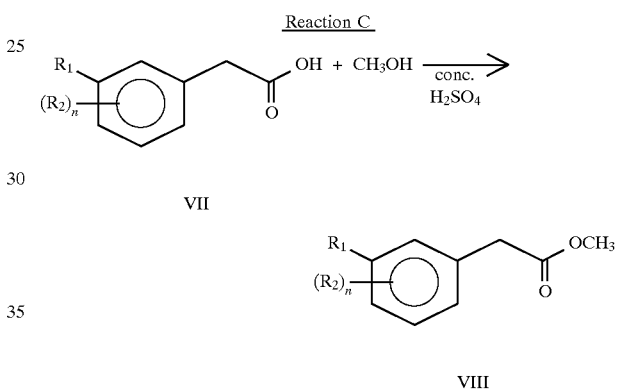

In Reaction D, compound VIII is reacted with the substituted or unsubstituted 1-indanone represented by graphic formula IX in the presence of sodium hydride resulting in a mixture of the tautomers represented by graphic formulae XA and XB. The tautomers are cyclized by heating, e.g., at about 70° C., in the presence of an acid such as phosphoric acid, to the indeno-fused naphthol represented by graphic formula I'.

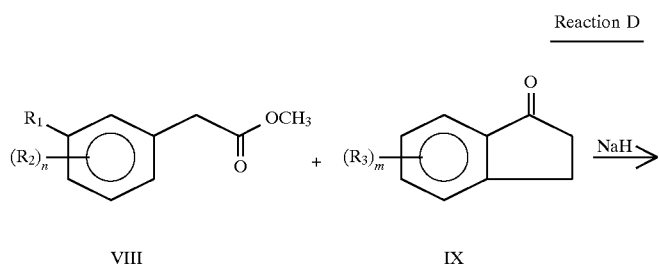

-continued
Reaction D

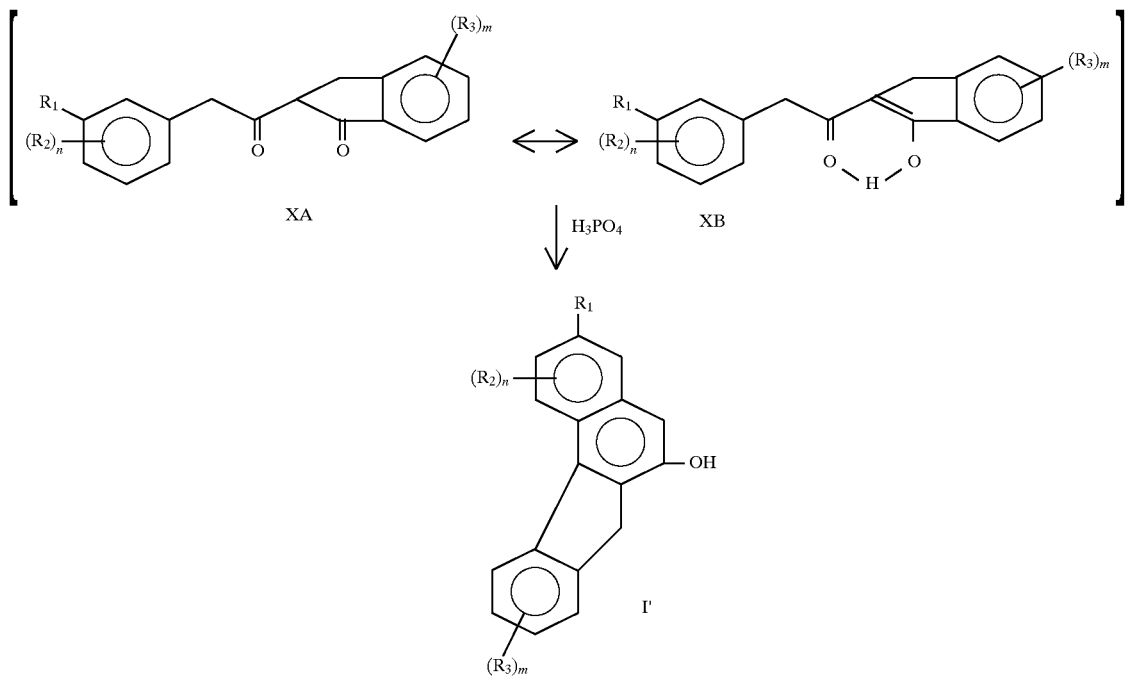

In Reaction E, the compound represented by graphic formula I' is coupled with a propargyl alcohol represented by graphic formula VI in the presence of a catalytic amount of an acid, e.g., p-toluene sulfonic acid in a suitable solvent such as chloroform to produce compounds represented by graphic formula Ia.

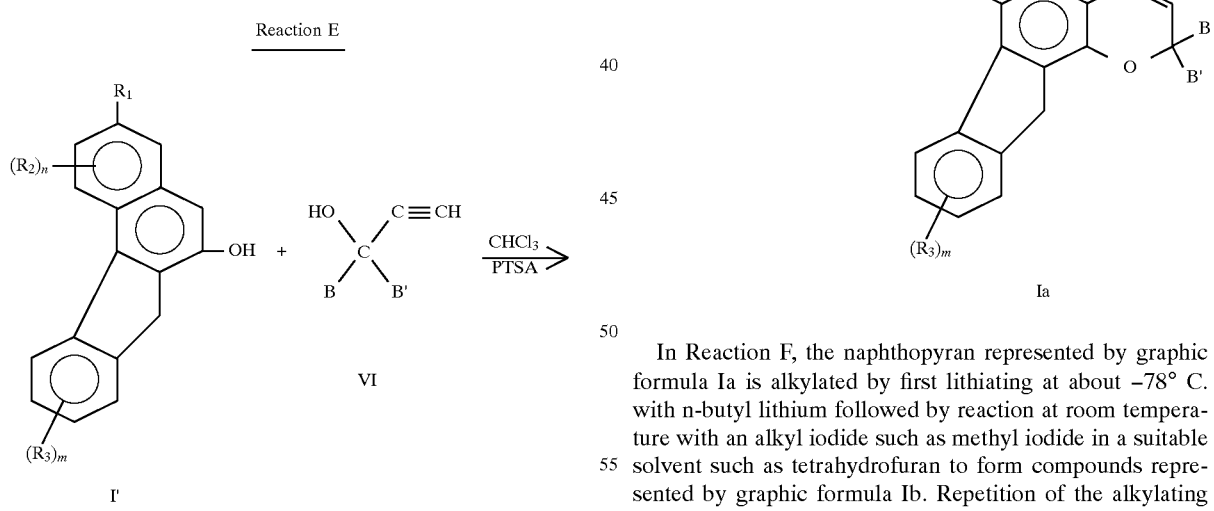

In Reaction F, the naphthopyran represented by graphic formula Ia is alkylated by first lithiating at about −78° C. with n-butyl lithium followed by reaction at room temperature with an alkyl iodide such as methyl iodide in a suitable solvent such as tetrahydrofuran to form compounds represented by graphic formula Ib. Repetition of the alkylating reactions using compound Ib produces the compounds represented by graphic formula Ic.

Reaction F

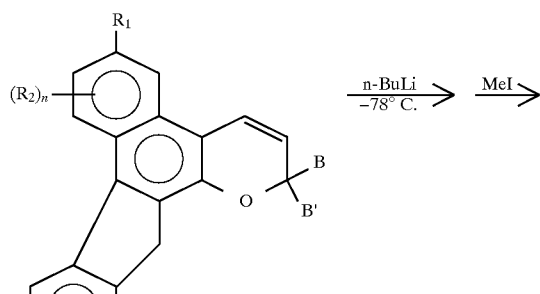

Ia

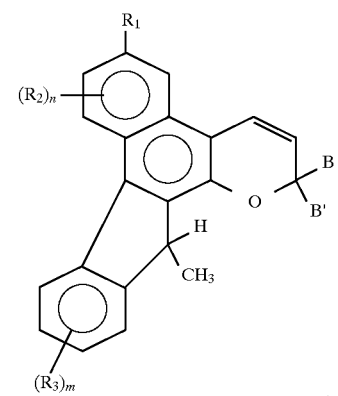

Ib

Reaction F
-continued

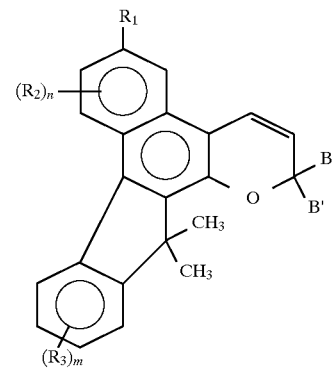

Ic

Compound Ia may be oxidized as depicted in Reaction G with benzyltrimethylammonium hydroxide in air to form the indanone naphthopyrans represented by graphic formula Id. Compound Id may be reduced via reaction with lithium aluminum hydride to form compounds represented by graphic formula Ie. Alternatively, compound Id may be reacted with an alkyl lithium such as butyl lithium or methyl lithium to form compounds represented by graphic formula Ig wherein R' is an alkyl group.

Reaction G

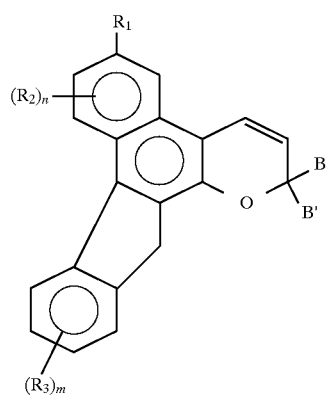

Ia

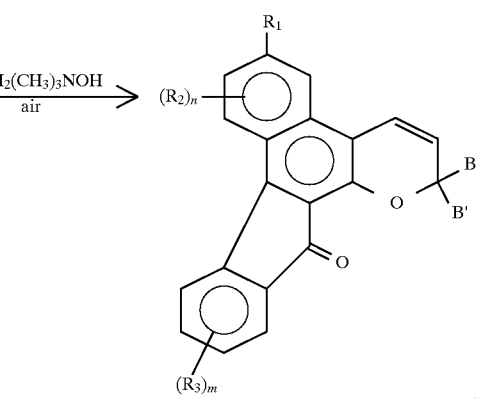

Id

-continued
Reaction G

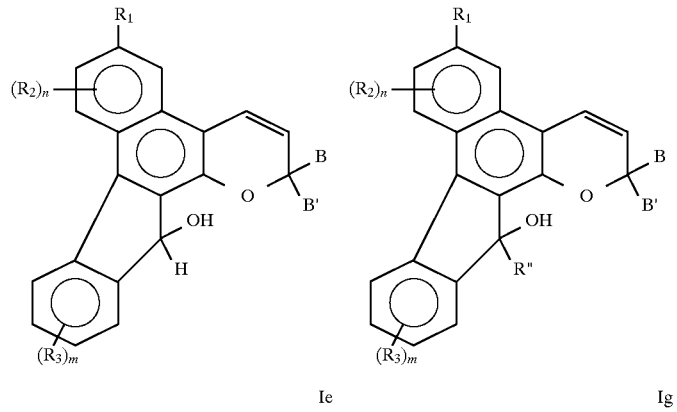

Ie                     Ig

Compounds represented by graphic formula I may be used in those applications in which organic photochromic substances may be employed, such as optical lenses, e.g., vision correcting ophthalmic lenses and plano lenses, face shields, goggles, visors, camera lenses, windows, automotive windshields, aircraft and automotive transparencies, e.g., T- roofs, sidelights and backlights, plastic films and sheets, textiles and coatings, e.g., coating compositions such as paints, and verification marks on security documents, e.g., documents such as banknotes, passports and drivers, licenses for which authentication or verification of authenticity may be desired. The indeno-fused naphtho[2,1-b] pyrans represented by graphic formula I exhibit color changes from colorless to colors ranging from yellow to orange.

Examples of contemplated naphthopyran compounds within the scope of the invention include the following:

(a) 6-methoxy-2,2-diphenyl-2,13-dihydro-indeno[1',2':4,3]naphtho[2,1-b]pyran;

(b) 6,7-dimethoxy-2,2-diphenyl-2,13-dihydro-indeno[1',2':4,3]naphtho[2,1-b]pyran;

(c) 6,7-dimethoxy-2-(2-fluorophenyl)-2-(4-methoxyphenyl)-2,13-dihydro-indeno[1'2':4,3]naphtho[2,1-b]pyran;

(d) 6,7-dimethoxy-2,2-diphenyl-13-methyl-2,13-dihydro-indeno[1',2':4,3]naphtho[2,1-b]pyran;

(e) 6,7-dimethoxy-2,2-diphenyl-13-oxo-2,13-dihydro-indeno-[1'2':4,3]naphtho[2,1-b]pyran;

(f) 6,7-dimethoxy-2,2-diphenyl-13-hydroxy-13-butyl-2,13-dihydro-indeno[1'2':4,3]naphtho[2,1-b]pyran;

(g) 6,7-dimethoxy-2,2-diphenyl-13-hydroxy-13-methyl-2,13-dihydro-indeno[1',2':4,3]naphtho[2,1-b]pyran;

(h) 6,7-dimethoxy-2,2-diphenyl-13-hydroxy-2,13-dihydro-indeno[1',2':4,3]naphtho[2,1-b]pyran; and (i) 6,7-dimethoxy-2,2-diphenyl-13,13-dimethyl-2,13-dihydro-indeno[1',2':4,3]naphtho[2,1-b]pyran.

Examples of contemplated naphthols within the scope of the invention include the following:

(a) 3-methoxy-7H-benzo[c]floren-6-ol; and (b) 2,3-dimethoxy-7H-benzo[c]fluoren-6-ol.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers (or substances containing same) and which color when activated to an appropriate hue. The photochromic compounds of the present invention may be associated with, e.g., incorporated in, i.e., dissolved or dispersed in, a polymeric organic host material used to prepare photochromic articles.

Other than where otherwise indicated, all numbers expressing wavelengths, quantities of ingredients or reaction conditions used herein are to be understood as modified in all instances by the term "about".

Examples of complementary organic photochromic compounds include other naphthopyrans, chromenes and oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, spiro(benzindoline) naphthopyrans, spiro(indoline)benzopyrans, spiro(indoline) naphthopyrans, spiro(indoline)quinopyrans, spiro(indoline) pyrans, spiro(indoline)naphthoxazines, spiro(indoline) pyridobenzoxazines, spiro(benzindoline) pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,981; 5,274,132; 5,384,077; 5,405,958; 5,429,774; 5,458,814; 5,466,398; 5,514,817; 5,552,090; 5,552,091; 5,565,147; 5,573,712; 5,578,252; 5,645,767 and Japanese Patent Publication 62/195383. Spiro(indoline) pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3- thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates re obtained by taking the ratios of the tristimulus values to their sum, e.g., x=X/(X+Y+Z) and y=Y/(X+Y+Z). Color as described in the CIE system can be plotted on a chromaticity diagram, usually a plot of the chromaticity coordinates x and y. See pages 47–52 of Principles of Color Technology, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be associated with, applied to or incorporated within a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating or film placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be dissolved in an organic solvent or present in an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc. Examples of polymeric organic host materials are polymers prepared from individual monomers or mixtures of monomers selected from the following groups:

(a) diacrylate or dimethacrylate compounds represented by graphic formula XI:

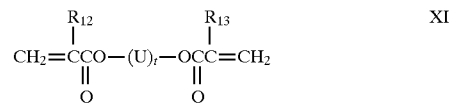

wherein $R_{12}$ and $R_{13}$ may be the same or different and are hydrogen or methyl, and U is methylene ($CH_2$), and t is an integer of from 1 to 20;

(b) diacrylate or dimethacrylate compounds represented by graphic formula XII:

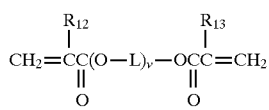

wherein L is $CH_2CH(R_{13})$, or $(CH_2)s$ wherein s is an integer selected from the group consisting of 1, 3 and 4, and v is an integer of from 1 to 50; and (c) an acrylate or a methacrylate compound having an epoxy group represented by graphic formula XIII:

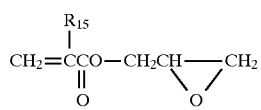

wherein $R_{15}$ is hydrogen or methyl.

In graphic formulae XI, XII and XII, like letters used with respect to the definitions of different substituents have the same meaning.

Examples of diacrylate or dimethacrylate compounds, i.e., di(meth)acrylates, represented by graphic formulae XI include butanediol di(meth)acrylate, hexanediol di(meth)acrylate, and nonanediol di(meth)acrylate; examples of compounds represented by graphic formula XII include diethylene glycol dimethacrylate, triethylene glycol dimethacrylate, etc., butanediol dimethacrylate and poly(oxyalkylene dimethacrylates), e.g., polyethylene glycol (600) dimethacrylate. Examples of acrylate or methacrylate compounds represented by graphic formula XIII include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XI, XII and XIII, bis(allyl carbonate) monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_2$ alkyl methacrylates), such as poly(methyl methacrylate), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The present invention is more particularly described in the following examples which are intended as illustrative only, since numerous modifications and variations therein will be apparent to those skilled in the art.

EXAMPLE 1

Step 1

4-Methoxyphenylacetic acid (80 grams, 0.48 mole) was mixed with methanol (300 milliliters (mL)) and 2 mL of concentrated sulfuric acid in a reaction flask equipped with a Dean-Stark trap, condenser and magnetic stirrer. The reaction mixture was maintained at reflux temperature overnight. After cooling, the solvent (methanol) was removed on a rotary evaporator. The product was dissolved in ether, washed with water three times and dried over anhydrous sodium sulfate. The ether was removed on a rotary evaporator leaving 85.0 grams of a colorless oil identified as methyl 3-methoxyphenylacetate.

Step 2

The 3-methoxyphenylacetate from Step 1 (18.0 grams, 0.1 mole) was mixed with sodium hydride (8.0 grams, 0.2 mole of a 60% dispersion in mineral oil) and stirred in tetrahydrofuran (150 mL) in a 500 mL 3-necked reaction flask equipped with a condenser, mechanical stirrer and addition funnel. 1-Indanone (13.2 grams, 0.1 mole) dissolved in tetrahydrofuran (100 mL) was added slowly to the slurry. After all of the ketone was added, the reaction mixture was heated at 40°–50° C. for two hours. The resulting mixture was poured into a 4 liter beaker containing a mixture of ice and hydrochloric acid resulting in the formation of a precipitate. The precipitate was filtered, air dried and dissolved in a mixture of chloroform in an aqueous potassium hydroxide solution. The resulting mixture was filtered, combined with the aqueous layer, acidified, filtered again and air dried to yield the product identified as 2-(3-methoxyphenyl acetyl)-1-indanone.

Step 3

All of the indanone from Step 2 was mixed with o-phosphoric acid (85 weight percent, 50 mL) and heated at about 70° C. for four to five hours to cyclize the ketone. The resulting deep red reaction mixture was poured into 1 liter of water yielding a brownish precipitate. The precipitate was filtered and air dried, yielding 3.5 grams of product identified as 3-methoxy-7H-benzo[c]fluoren-6-ol.

Step 4

The fluorenol from Step 3 (1 gram, 3.8 millimole) was mixed with 1,1-diphenyl-2-propyn-1-ol (1 gram, 5 millimole) and chloroform (50 mL) in a reaction flask. The reaction was catalyzed by the addition of p-toluene sulfonic acid (0.1 gram), and the mixture was stirred at 45°–50° C. for four hours. The mixture was cooled to room temperature, washed with water and dried over anhydrous sodium sulfate. The solvent (chloroform) was removed on a rotary evaporator, and the desired product was purified through a silica column and crystallized from ether to yield 0.4 gram of the product. A nuclear magnetic resonance (NMR) spectrum showed the product to have a structure consistent with 6-methoxy-2,2-diphenyl- 2,13-dihydro-indeno[1'2':4,3]naphtho[2,1-b]pyran.

EXAMPLE 2

Step 1

Step 1 of Example 1 was repeated except that 3,4-methoxyphenyl acetic acid was used instead of 4-methoxyphenyl acetic acid to produce methyl 3,4-dimethoxyphenylacetate.

Step 2

The methyl 3,4-dimethoxyphenylacetate (84 grams, 0.4 mole) from Step 1 was mixed with sodium hydride (32 grams, 0.8 mole, 60 percent dispersion in mineral oil), tetrahydrofuran (THF) (200 mL) and dry ether (150 mL) in a three-necked reaction flask equipped with a condenser, mechanical stirrer and addition funnel. 1-Indanone (65 grams, 0.4 mole) dissolved in tetrahydrofuran (200 mL) was added slowly to the mixture. After all the ketone was added, the reaction mixture was stirred for one hour at room temperature. The reaction mixture was poured into a mixture of ice and hydrochloric acid. The solvents, ether and tetrahydrofuran, were evaporated to leave a gum-like product. The product was dissolved in chloroform. Concentrated potassium hydroxide solution was added to the chloroform solution and a precipitate formed. Following filtration and a chloroform wash, the precipitate and potassium hydroxide filtrate were recombined and acidified with hydrochloric acid yielding a product identified as 2-(3,4-dimethoxyphenylacetyl)-1-indanone. The indanone was filtered, air dried and used directly in the next step.

Step 3 All of the indanone from Step 2 was mixed with an 85 percent solution of phosphoric acid (200 mL) and heated to 70° C. for six hours. The reaction mixture was poured into ice water to produce a precipitate. The precipitate was filtered, washed several times with water and air dried yielding 41 grams of a product identified as 2,3-dimethoxy-7H-benzo[c]fluoren-6-ol.

Step 4

The fluorenol from Step 3 (20 grams, 68.5 millimole) was mixed with 1,1-diphenyl-2-propyn-1-ol (16.6 grams, 80 millimole) and chloroform (150 mL) in a reaction flask. The reaction was catalyzed by the addition of p-toluene sulfonic acid (0.2 gram). The reaction mixture was kept at 45°–50° C. for six hours. Following a water wash and drying over anhydrous sodium sulfate, the chloroform was evaporated. The desired product crystallized from ether yielding 10 grams of product having a melting point of 200°–201° C. An NMR spectrum showed the product to have a structure consistent with 6,7-dimethoxy-2,2-diphenyl-2,13-dihydro-indeno[1'2':4,3]naphtho[2,1-b]pyran.

EXAMPLE 3

The process of Example 2 was followed except that in Step 4 1-(2-fluorophenyl)-1-(4-methoxyphenyl)-2-propyn-1-ol was used instead of 1,1-diphenyl-2-propyn-1-ol. An NMR spectrum showed the resulting product have a structure consistent with 6,7-dimethoxy-2-(2-fluorophenyl)-2-(4-methoxyphenyl)-2,13-dihydro-indeno[1',2':4,3]naphtho[2,1-b]pyran having a melting point of 195°–196° C.

EXAMPLE 4

6,7-Dimethoxy-2,2-diphenyl-2,13-dihydro-indeno[1',2':4,3]naphtho[2,1-b]pyran produced in Example 2 (5 grams, 10.4 millimoles) was mixed with tetrahydrofuran (50 mL) in a reaction flask. The solution was cooled to −78° C. and n-butyl lithium (10 mL, 2.5 molar solution in hexane) was slowly injected via a syringe, and the reaction mixture was stirred for 15 minutes. Methyl iodide (1.6 mL, 25 millimoles) was injected into the reaction mixture. After warming to room temperature, the reaction mixture was poured into a beaker containing ether and hydrochloric acid. The ether layer was separated, washed once with a sodium sulfate solution, washed twice with water and dried over anydrous sodium sulfate. Crystallization from an ether/hexane mixture yielded 2.5 grams of the product having a melting point of 187°–188° C. An NMR spectrum showed the product to have a structure consistent with 6,7-dimethoxy-2,2-diphenyl-13-methyl-2,13-dihydro-indeno[1',2':4,3]naphtho[2,1-b]pyran.

EXAMPLE 5

The procedure of Example 4 was followed except that the product of Example 4 was used in place of the product of Example 2, 2 mL of n-butyl lithium was used instead of 10 mL and 0.7 mL of methyl iodide was used instead of 1.6 mL. The recovered product, 0.6 gram, had a melting point of 161°–162° C. An NMR spectrum showed the product to have a structure consistent with 6,7-dimethoxy-2,2-diphenyl-13,13-dimethyl-2,13-dihydro-indeno[1',2':4,3]naphtho[2,1-b]pyran.

EXAMPLE 6

The indenonaphthopyran produced in Example 2 (1.0 gram) was mixed with tetrahydrofuran (40 mL) in a reaction flask. Benzyltrimethylammonium hydroxide (2.0 mL, 40 weight percent aqueous solution) was added to the mixture and vigorously stirred in air for two hours. The resulting mixture was poured into a beaker containing water and acidified with hydrochloric acid to form an orange precipitate. The precipitate was filtered, washed with water and air dried yielding 0.9 gram of the product. An NMR spectrum showed the product to have a structure consistent with 6,7-dimethoxy-2,2-diphenyl-13-oxo-2,13-dihydro- indeno[1',2':4,3]naphtho[2,1-b]pyran.

EXAMPLE 7

The indeno-fused naphthopyran produced in Example 6 (1.0 gram, 2 millimole) was mixed with tetrahydrofuran (20 mL) in a reaction flask, and the solution was cooled to 0° C. n-Butyl lithium (5 mL, 1.0 molar solution in hexane) was injected into the solution via a syringe and the resulting mixture was stirred for five minutes. The reaction mixture was poured into a beaker containing ether and hydrochloric acid. The ether layer was separated, washed twice with water and dried over anhydrous sodium sulfate. Crystallization from an ether/hexane mixture yielded 0.4 gram of the product having a melting point of 235°–236° C. An NMR spectrum showed the product to have a structure consistent with 6,7-dimethoxy-2,2-diphenyl-13-hydroxy-13-butyl-2,13-dihydro-indeno[1',2':4,3]naphtho[2,1-b]pyran.

EXAMPLE 8

The process of Example 7 was followed except that methyl lithium was used instead of butyl lithium. The recovered product had a melting point of 228°–230° c. An NMR spectrum showed the product to have a structure consistent with 6,7-dimethoxy-2,2-diphenyl-13-hydroxy-13-methyl-2,13-dihydro-indeno[1',2':4,3]naphtho[2,1-b]pyran.

EXAMPLE 9

The indenone-fused naphthopyran produced in Example 6 was mixed with lithium aluminum hydride and THF in a reaction flask. The reaction mixture was purified, and the recovered product had a melting point of 212°–213° C. An NMR spectrum showed the product to have a structure consistent with 6,7-dimethoxy-2,2-diphenyl-13-hydroxy-2,13-dihydro- indeno[1',2':4,3]naphtho[2,l-b]pyran.

EXAMPLE 10

PART A

Testing was done with the photochromic compounds described in Examples 1–5 and 7–9 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours and then lower it to 60° C. for at least 2 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.90° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. A collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (ΔOD) was determined by inserting a test square in the bleached state into the sample holder, adjusting the transmittance scale to 100% opening the shutter from the Xenon lamp to provide ultraviolet radiation to change the test square from the bleached state to an activated (i.e., darkened) state, measuring the transmittance in the activated state, and calculating the change in optical density according to the formula: ΔOD=log(100/%Ta), where %Ta is the percent transmittance in the activated state and the logarithm is to the base 10.

The optical properties of the photochromic compound in the test squares are reported in Table 1. The Δ OD/Min, which represents the sensitivity of the photochromic compound's response to UV light, was measured over the first five (5) seconds of UV exposure, then expressed on a per minute basis. The saturation optical density (Δ OD@ Sat) was taken under identical conditions as the Δ OD/Min, except UV exposure was continued for 20 minutes. The lambda max (Vis) is the wavelength in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The lambda (λ) max (UV) is the wavelength in the ultraviolet range closest to the visible spectrum at which the absorption of the photochromic compound occurs. This absorption was also determined with the same spectrophotometer. The bleach rate (T ½) is the time interval in seconds for the absorbance of the activated form of the photochromic compound in the test squares to reach one half the highest absorbance at room temperature (75° F., 23.90° C.) after removal of the source of activating light. Results for the photochromic compounds tested are listed in Table 1

TABLE 1

| Example Compounds | (λ) max (VIS) | (λ) max (UV) | ΔOD/MIN sensitivity | ΔOD @ saturation | Bleach T ½ |
| --- | --- | --- | --- | --- | --- |
| 1 | 437 | 366 | 0.52 | 0.38 | 42 |
| 2 | 443 | 387 | 0.48 | 0.44 | 51 |

TABLE 1-continued

| Example Compounds | (λ) max (VIS) | (λ) max (UV) | ΔOD/MIN sensitivity | ΔOD @ saturation | Bleach T ½ |
|---|---|---|---|---|---|
| 3 | 464 | 385 | 0.48 | 1.22 | 227 |
| 4 | 442 | 356 | 0.43 | 0.38 | 62 |
| 5 | 446 | 358 | 0.39 | 0.37 | 58 |
| 7 | 445 | 356 | 0.41 | 0.23 | 38 |
| 8 | 459 | 361 | 0.41 | 0.25 | 35 |
| 9 | 469 | 359 | 0.28 | 0.17 | 31 |

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formula:

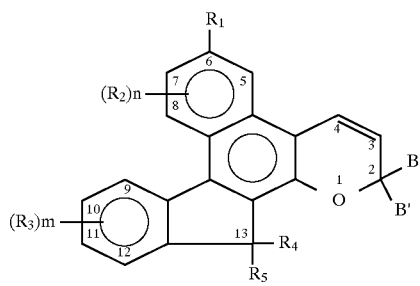

I wherein, (a) $R_1$ is $C_1$–$C_6$ alkoxy;

(b) each $R_2$ is $C_1$–$C_6$ alkyl, $C_1$–$C_6$ alkoxy, chloro, or fluoro, and n is the integer 0, 1, or 2;

(c) each $R_3$ is $C_1$–$C_6$ alkyl, chloro or fluoro, and m is the integer 0, 1 or 2;

(d) $R_4$ and $R_5$ together form an oxo group, or $R_4$ and $R_5$ are each hydrogen, hydroxy, $C_1$–$C_6$ alkyl, $C_3$–$C_7$ cycloalkyl, allyl, phenyl, mono-substituted phenyl, benzyl, mono-substituted benzyl, or $R_4$ and $R_5$ are each the group, —$OR_6$, wherein $R_6$ is $C_1$–$C_6$ alkyl, phenyl ($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl or allyl, each of said phenyl and benzyl group substituents being $C_1$–$C_6$ alkyl or $C_1$–$C_6$ alkoxy; and (e) B and B' are each selected from the group consisting of:

(i) the unsubstituted, mono-, di-, and tri-substituted aryl groups, phenyl and naphthyl;

(ii) the unsubstituted, mono-, and di-substituted heteroaromatic groups pyridyl, furanyl, benzofuran-2-yl, benzofuran-3-yl, thienyl, benzothien-2-yl, benzothien-3-yl, said aryl and heteroaromatic substituents in (e)(i) and (ii) being selected from the group consisting of hydroxy, amino, mono($C_1$–$C_6$) alkylamino, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$) alkoxy($C_1$–$C_4$)alkyl, acryloxy, methacryloxy, chloro and fluoro;

(iii) the groups represented by the following graphic formulae:

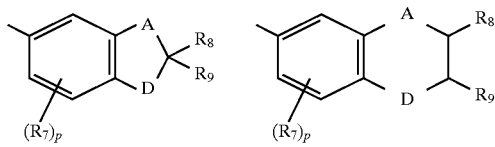

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl, and $C_2$–$C_6$ acyl; each $R_7$ is $C_1$–$C_6$ alkyl, $C_1$–$C_6$ alkoxy, hydroxy, chloro or fluoro; $R_8$ and $R_9$ are each hydrogen or $C_1$–$C_6$ alkyl; and p is the integer 0, 1, or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)-cycloalkyl, chloro ($C_3$–$C_6$)cycloalkyl and fluoro($C_3$–$C_6$)cyclo-alkyl; and (v) the group represented by the following graphic formula:

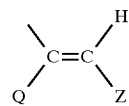

wherein Q is hydrogen or $C_1$–$C_4$ alkyl and Z is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, fluoro, or chloro; or (vi) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein, (a) $R_1$ is $C_1$–$C_3$ alkoxy;

(b) $R_2$ is $C_1$–$C_3$ alkyl, $C_1$–$C_3$ alkoxy, or fluoro, and n is the integer 0 or 1;

(c) $R_3$ is $C_1$–$C_3$ alkyl or fluoro, and m is the integer 0 or 1;

(d) $R_4$ and $R_5$ are each selected from the group consisting of hydrogen, hydroxy, $C_1$–$C_4$ alkyl, $C_3$–$C_6$ cycloalkyl, chloro, fluoro and the group, —$OR_6$, wherein $R_6$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl or $C_1$–$C_3$ fluoroalkyl; and (e) B and B' are each selected from the group consisting of:

(i) phenyl, mono-substituted phenyl, and di-substituted phenyl;

(ii) the unsubstituted, mono-, and di-substituted heteroaromatic groups furanyl, benzofuran-2-yl, thienyl, and benzothien-2-yl, said phenyl and heteroaromatic substituents in (e)(i) and (ii) being selected from the group consisting of hydroxy, amino, mono($C_1$–$C_3$)alkyl-amino, di($C_1$–$C_3$)

alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;

(iii) the groups represented by the following graphic formulae:

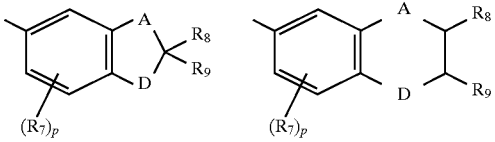

wherein A is carbon and D is oxygen, $R_7$ is $C_1$–$C_3$ alkyl or $C_1$–$C_3$ alkoxy, $R_8$ and $R_9$ are each hydrogen or $C_1$–$C_4$ alkyl; and p is the integer 0 or 1;

(iv) $C_1$–$C_4$ alkyl; and (v) the group represented by the following graphic formula:

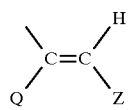

wherein Q is hydrogen or methyl and Z is phenyl or mono- substituted phenyl, said phenyl substituent being selected from the group consisting of $C_1$–$C_3$ alkyl, $C_1$–$C_3$ alkoxy, and fluoro; or (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, each of said fluoren-9-xylidene substituents being selected from the group consisting of $C_1$–$C_3$ alkyl, $C_1$–$C_3$ alkoxy, fluoro and chloro.

3. The naphthopyran compound of claim 2 wherein, (a) $R_2$ is $C_1$–$C_3$ alkyl or $C_1$–$C_3$ alkoxy, and n is the integer 0 or 1;

(b) m is 0;

(c) $R_4$ and $R_5$ are each hydrogen, hydroxy, $C_1$–$C_4$ alkyl, or the group, —$OR_6$, wherein $R_6$ is $C_1$–$C_3$ alkyl; and (d) B and B' are each selected from the group consisting of phenyl, mono-, and di-substituted phenyl, unsubstituted, mono-, and di-substituted heteroaromatic groups furanyl, benzofuran-2-yl, thienyl, and benzothien-2-yl, each of said phenyl and heteroaromatic substituents being selected from the group consisting of hydroxy, $C_1$–$C_3$ alkyl, $C_1$–$C_3$ alkoxy, fluoro and chloro; and the group represented by the following graphic formula:

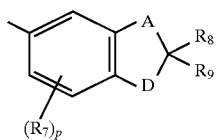

wherein A is carbon and D is oxygen, $R_7$ is $C_1$–$C_3$ alkyl or $C_1$–$C_3$ alkoxy, $R_8$ and $R_9$ are each hydrogen or $C_1$–$C_3$ alkyl, and p is the integer 0 or 1; or B and B' taken together form fluoren-9-ylidene, adamantylidene, bornylidene, norbornylidene, or bicyclo(3.3.1)nonan-9-ylidene.

4. A naphthopyran compound selected from the group consisting of:

(a) 6-methoxy-2,2-diphenyl-2,13-dihydro-indeno[1',2':4,3]naphtho[2,1-b]pyran;

(b) 6,7-dimethoxy-2,2-diphenyl-2,13-dihydro- indeno[1',2':4,3]naphtho[2,1-b]pyran;

(c) 6,7-dimethoxy-2-(2-fluorophenyl)-2-(4-ethoxyphenyl)-2,13-dihydro-indeno[1'2':4,3]naphtho[2,1-b]pyran;

(d) 6,7-dimethoxy-2,2-diphenyl-13-methyl-2,13-dihydro-indeno[1',2':4,3]naphtho[2,l-b]pyran;

(e) 6,7-dimethoxy-2,2-diphenyl-13-oxo-2,13-dihydro-indeno[1'2':4,3]naphtho[2,1-b]pyran;

(f) 6,7-dimethoxy-2,2-diphenyl-13-hydroxy-13-butyl-2,13-dihydro-indeno[1'2':4,3]naphtho[2,1-b]pyran;

(g) 6,7-dimethoxy-2,2-diphenyl-13-hydroxy-13-methyl-2,13-dihydro-indeno[1',2':4,3]naphtho[2,1-b]pyran;

(h) 6,7-dimethoxy-2,2-diphenyl-13-hydroxy-2,13-dihydro-indeno[1',2':4,3]naphtho[2,1-b]pyran; and (i) 6,7-dimethoxy-2,2-diphenyl-13,13-dimethyl-2,13-dihydro-indeno[1',2':4,3]naphtho[2,1-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance (s) is incorporated or applied.

9. The photochromic article of claim 8 wherein the article is a lens.

10. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)-benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance (s) is incorporated or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 2, and (b) at least one other organic photochromic compound having at least one activated absorption maxima within the range of between about 400 and 700 nanometers.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *

UNITED STATES PATENT AND TRADEMARK OFFICE
CERTIFICATE OF CORRECTION

PATENT NO.    : 5,869,658
DATED         : February 9, 1999
INVENTOR(S)   : J. Lin et al.

It is certified that error appears in the above-identified patent and that said Letters Patent is hereby corrected as shown below:

Column 24, claim 4 (c),
Line 8, "ethoxyphenyl" should be -- methoxyphenyl. --

Signed and Sealed this

Eleventh Day of December, 2001

Attest:

NICHOLAS P. GODICI
*Attesting Officer*    *Acting Director of the United States Patent and Trademark Office*